United States Patent
Bracht

(10) Patent No.: US 7,056,528 B1
(45) Date of Patent: Jun. 6, 2006

(54) TRANSDERMAL THERAPEUTIC SYSTEM CONTAINING TULOBUTEROL HYDROCHLORIDE FOR ADMINISTERING THE BRONCHODILATOR TULOBUTEROL VIA THE SKIN

(75) Inventor: Stefan Bracht, Ochtendung (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 248 days.

(21) Appl. No.: 10/110,014

(22) PCT Filed: Oct. 6, 2000

(86) PCT No.: PCT/EP00/09788

§ 371 (c)(1),
(2), (4) Date: Jun. 10, 2002

(87) PCT Pub. No.: WO01/28531

PCT Pub. Date: Apr. 26, 2001

(30) Foreign Application Priority Data

Oct. 16, 1999 (DE) .............................. 199 50 066

(51) Int. Cl.
*A61F 13/00* (2006.01)
*A61F 13/02* (2006.01)

(52) U.S. Cl. ..................... 424/449; 424/443; 424/448

(58) Field of Classification Search .............. 424/443, 424/447, 448, 449, 444, 445, 446
See application file for complete search history.

(56) References Cited

U.S. PATENT DOCUMENTS

| 5,254,348 | A |   | 10/1993 | Hoffmann et al. ........... 424/449 |
| 5,312,627 | A |   | 5/1994  | Stroppolo et al. |
| 5,571,530 | A |   | 11/1996 | Nakano et al. |
| 5,639,472 | A | * | 6/1997  | Yamamoto et al. .......... 424/449 |
| 5,932,227 | A | * | 8/1999  | Higo et al. .................. 424/401 |
| 6,117,447 | A | * | 9/2000  | Nakano et al. .............. 424/448 |
| 6,231,885 | B1 | * | 5/2001 | Carrara ....................... 424/448 |
| 6,375,963 | B1 | * | 4/2002 | Repka et al. ................ 424/402 |

FOREIGN PATENT DOCUMENTS

| DE | 40 02 281    | 8/1991 |
| EP | 0 439 180 A  | 7/1991 |
| EP | 0 922 453 A  | 6/1999 |
| EP | 0 943 330 A1 | 9/1999 |

OTHER PUBLICATIONS

Patent Abstracts of Japan, Publ. No. 63010716, Jan. 18, 1998, "Beta-Stimulation Agent for External Use", Makino Yuji et al.

* cited by examiner

*Primary Examiner*—James M. Spear
(74) *Attorney, Agent, or Firm*—Birch, Stewart, Kolasch & Birch, LLP

(57) ABSTRACT

A transdermal therapeutic system comprising a largely water vapor-impermeable backing layer, at least one active substance-containing matrix layer comprising the active substance tulobuterol, as well as a removable protective layer, is characterized in that said matrix is built-up on the basis of polyacrylate pressure-sensitive adhesives and contains tulobuterol in the form of its salt tulobuterol hydrochloride as active substance.

26 Claims, 1 Drawing Sheet

TRANSDERMAL THERAPEUTIC SYSTEM CONTAINING TULOBUTEROL HYDROCHLORIDE FOR ADMINISTERING THE BRONCHODILATOR TULOBUTEROL VIA THE SKIN

This application is the national phase under 35 U.S.C. § 371 of PCT International Application No. PCT/EP00/09788 which has an International filing date of Oct. 6, 2000.

BACKGROUND OF THE INVENTION

1. Field of the Invention

This invention relates to a transdermal therapeutic system containing tulobuterol hydrochloride, which system enables the administration of the bronchodilator tulobuterol via the skin. The transdermal medicinal preparation is suitable for treatment of asthmatic diseases.

2. Description of the Related Art

Tulobuterol is a medicinal agent from the group of the β-sympathomimetics. It is predominantly active on the $β_2$-receptors of non-striated muscles, for example, in the bronchi. Due to its having the properties of reducing the bronchial muscular tone and effecting a relaxation of the bronchial muscles, tulobuterol is being used in the therapy of asthmatic diseases.

Apart from oral administration forms, from the literature there are also known transdermal application systems for tulobuterol which can be successfully utilized in asthma therapy. Transdermal therapeutic systems containing tulobuterol have been described, for example, in JP 63-10716 A, U.S. Pat. No. 5,254,348, U.S. Pat. No. 5,312,627, U.S. Pat. No. 5,571,536 and U.S. Pat. No. 5,639,472.

U.S. Pat. No. 5,254,348 discloses a transdermal therapeutic system the tulobuterol-containing matrix of which is built-up on the basis of a styrene-1,3-diene-styrene block copolymer or a styrene-isoprene-styrene block copolymer.

U.S. Pat. No. 5,312,627 describes a transdermal therapeutic system suitable for administering active substances having bronchodilatory action, e.g. tulobuterol. As a matrix polymer, polyisobutylene is used.

In U.S. Pat. No. 5,571,530 there is likewise described a percutaneous composition comprising the active substance tulobuterol, with the active substance being present in a polymer matrix made up of a mixture of polyisobutylenes.

From U.S. Pat. No. 5,639,472 there is known a tulobuterol-containing composition suitable for percutaneous absorption. It is characterized by the fact that tuluburetol is present both in dissolved as well as in crystalline form in the pressure-sensitive adhesive layer of the plaster.

Finally, in EP 0 922 453 A2 there is disclosed a device for the percutaneous administration of tulobuterol. This administration form comprises a pressure-sensitive adhesive acrylate layer containing at least 5%-wt. of tulobuterol as free active substance base in completely dissolved condition. The active substance remains dissolved so that there is no loss of action by crystallization.

A suggestion as to the possible use of salts of tulobuterol or even of the hydrochloride is not found in EP 0 922 453 A2.

In the above-described tulobuterol-containing transdermal therapeutic systems, tulobuterol is preferably utilized as a free base, the reason for this being that the free base on account of its hydrophobic character can be readily absorbed via the skin, whereas the salts of tulobuterol (e.g. tulobuterol hydrochloride) are more strongly hydrophile, which results in a poorer ability to penetrate the skin. For this reason tulobuterol hydrochloride has heretofore only been used for peroral therapy, but not for transdermal administration. Only U.S. Pat. No. 5,254,348 also mentions, in general terms, the pharmaceutically acceptable salts of tulobuterol, without, however, dealing in more detail with the problem of the hydrophilicity or of the poorer capacity for skin penetration of the salts.

Apart from its poorer capacity to penetrate the skin, the use of tulobuterol hydrochloride instead of the free base also affords some remarkable advantages. Firstly, it has been used in asthma therapy for a much longer time and on a far wider scale. This means that one is able to have recourse to considerably more extensive material relating to the toxicology and pharmacology of this active substance. Secondly, due to its being used world-wide on a larger scale, tulobuterol hydrochloride is obtainable on commercially more favourable conditions and from a greater number of sources of supply than the free base. It is also considered an advantage that tulobuterol hydrochloride is monographically described in the Japanese pharmacopoeia (JP XIII). Therefore—by contrast to the case of tulobuterol—there already exists a pharmaceutical quality standard which can be made use of for world-wide approval.

SUMMARY OF THE INVENTION

It was therefore the object of the present invention to provide a transdermal administration form which enables the administration of tulobuterol in the form of its salt tulobuterol hydrochloride, and which has the advantages entailed in the use of tulobuterol hydrochloride.

In addition, with such transdermal administration form the intention is to obtain skin permeation rates sufficient to ensure therapeutic application.

This object is surprisingly achieved by a transdermal therapeutic system according to the invention that has a structure comprising a largely water vapour-impermeable backing layer, at least one active substance-containing matrix layer and a removable protective layer. The pharmaceutical product according to the present invention contains tulobuterol in the form of its salt tulobuterol hydrochloride, the active substance being present in a polymer matrix that is built-up on the basis of polyacrylate pressure-sensitive adhesives.

DETAILED DESCRIPTION

Figure 1:
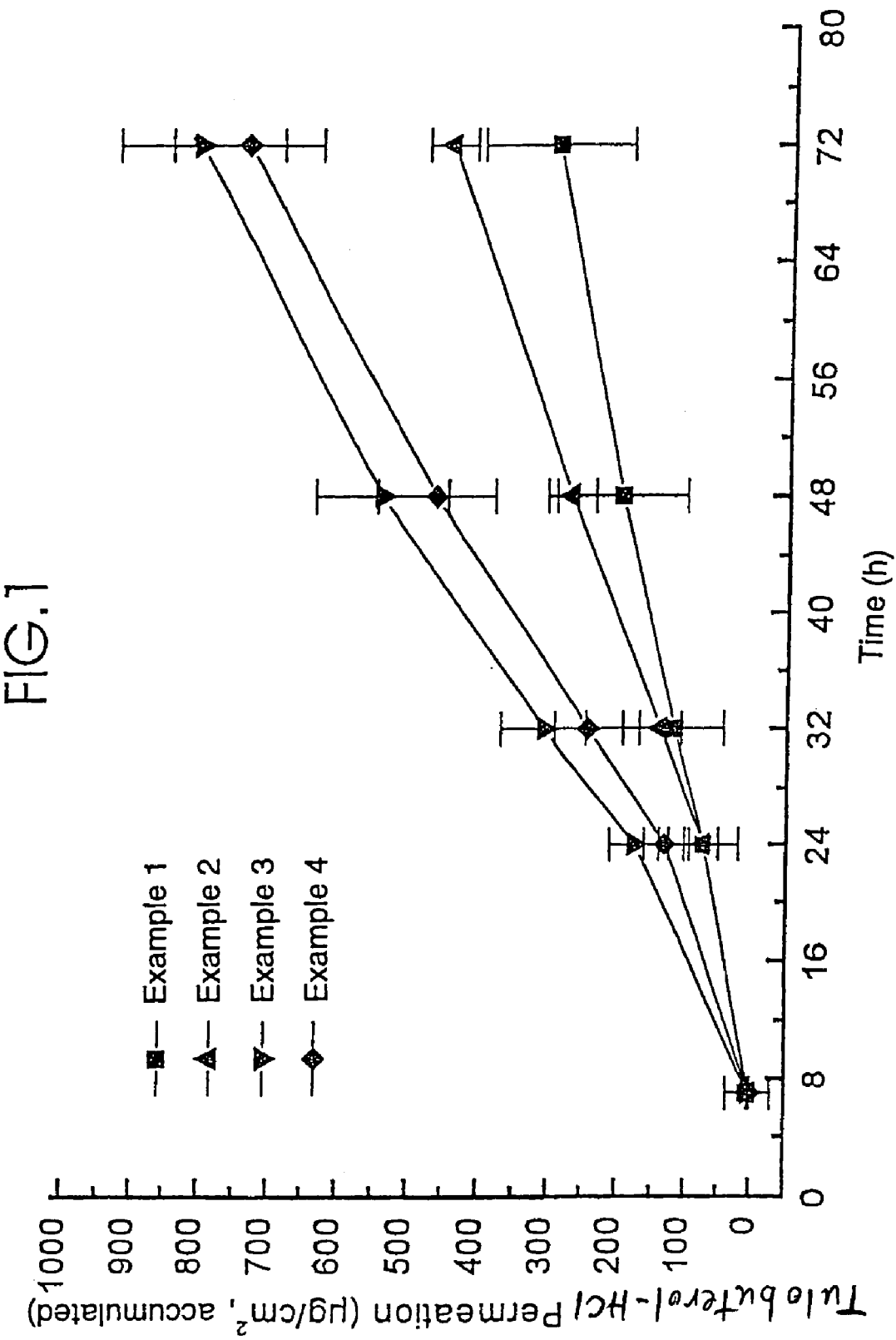
FIG. 1 shows a graph of the skin permeation of tolubuterol hydrochloride vs. time. The measurements were made using Examples 1 to 4 of Table 1.

Using tulobuterol hydrochloride, permeation rates of tulobuterol through human skin in vitro of more than 300 µg/cm$^2$·d were achieved by means of the application system according to the invention (cf. FIG. 1). In view of the fact that this substance is a relatively hydrophile salt form of an active agent, this is a surprisingly high permeation rate. It is assumed that tulobuterol hydrochloride, after its release from the TTS, permeates through the skin in the form of the free base tulobuterol.

By means of the administration form of the invention the daily doses of 0.5 to 6 mg of tulobuterol hydrochloride, which are usual in peroral administration, can be administered also via the transdermal route. Preferably, the transdermally administrable daily doses are in the range of 2 to 4 mg. The duration of application may extend up to three days and beyond. Thus, because of their active substance release characteristics the tulobuterol hydrochloride-containing transdermal therapeutic systems described herein are suitable for therapeutic use, for example, in cases of asthmatic diseases.

The active substance content of the matrix or the active substance concentration can be varied in wide ranges. In a preferred embodiment of the invention the mass content of tulobuterol hydrochloride lies in a range of 2.5 to 20%, preferably in a range of 5 to 10%, relative to the total mass of the active substance-containing matrix.

The base substance of the matrix layer or matrix layers, of which at least one has a content of tulobuterol hydrochloride, is built-up on the basis of polyacrylate pressure-sensitive adhesives. Polymers or polymer mixtures suitable for this purpose are known to those skilled in the art; to be considered are first of all polyacrylic, polymethacrylic, and polymethylmethacrylic acid and their derivatives as well as acrylic-acid ester copolymers. To adapt the mechanical properties of the matrix (e.g. cohesion, elasticity) to specific requirements, it is possible to add further polymers, for example, polyvinyl acetate, silicone polymers, polyisobutylenes, polyisoprene or styrene-containing block copolymers.

Particularly good results can be obtained with an embodiment of the invention wherein the polymer composition of the active substance-containing matrix contains a polymer having amino-functional groups in its side chains. The mass portion of this polymer amounts to 2 to 20%, preferably 10 to 16%, relative to the mass of the active substance-containing matrix. Preferably, as the polymer with amino-functional groups, a butyl methacrylate-(2-dimethyl-aminoethyl)-methyl methacrylate copolymer wherein the monomers are present in the molar ratio of 1:2:1 (=Eudragit® E-100) is used.

In the simplest case, the transdermal system according to the present invention comprises—besides the backing and the protective layer—only a single active substance-containing matrix layer. An especially preferred embodiment is, however, one characterized by a second matrix layer, likewise containing tulobuterol hydrochloride. The two active agent-containing layers are in this case laminated upon each other. The extent of the active substance load may be selected so as to be the same in both layers, but may also be chosen to be different. Typically, the two active substance-containing layers will have the same content of additives. For certain applications it may, however, be of advantage if the two layers differ from each other in respect of their content of additives. It is also possible to choose different polymer compositions for the matrix.

A further preferred embodiment variant provides that in the state immediately following manufacture, at least one of the matrix layers does not contain active substance. For example, in the case of a two-layer matrix the skin-facing matrix layer can be free of active agent, whereas the second matrix layer (reservoir layer) located directly thereabove contains tulobuterol hydrochloride. After manufacture and during the application period the active substance diffuses from the latter layer into the skin-facing, previously active substance-free matrix layer, from which the permeation into the skin can take place. The manufacture of the latter active substance patches is advantageous in terms of production logistics, one has to accept slightly lower rates of active substance release, however.

In certain cases it may be advantageous if the therapy with tulobuterol is combined with the therapy with one or more additional active substances. For this reason, there are provided further embodiments wherein at least one further matrix layer contains one or more further pharmaceutical active agents.

To improve the release of tulobuterol hydrochloride it is, in addition, possible to add skin permeation-enhancing additives to the matrix layers. Especially suitable for this purpose are saturated or unsaturated fatty acids, singly or in combination, preferably lauric acid, myristic acid or oleic acid. The matrix layer may have a content of 2 to 20%, preferably 5 to 10%, of fatty acids, relative to the total mass of the matrix layers. Combinations of different fatty acids may be used to advantage.

Suitable as permeation-enhancing additives are furthermore substances from the group of low-molecular mono- or polyvalent alcohols, fatty alcohols, fatty alcohol ethers, polyoxyethylated fatty alcohols, fatty acid esters (especially monoglycerides and monoesters with propylene glycol), as well as sorbitan fatty acid esters and polyoxyethylated sorbitan fatty acid esters.

Furthermore, the active substance-containing matrix layers may contain plasticizers, tackifiers, cohesion-promoting additives, stabilizers, fillers and similar additives. The substances suitable for this purpose are known to those skilled in the art.

According to a further preferred embodiment, the active substance-containing matrix of the tulobuterol hydrochloride-containing transdermal active substance patches has a weight per unit area of at least 120 g/m$^2$. Such above-average layer-thicknesses of the matrix ensure, in particular, a constant, high release rate over a period of more than 24 hours.

The materials which can be used for the substantially water-impermeable backing layer and for the detachable protective layer are known to those skilled in the art. For the backing layer, polymer films, above all polyester, are suitable which are characterized by particular strength and resistance to diffusion, but apart from these almost any other skin-tolerable plastics such as polyvinyl chloride, ethylene-vinyl acetate, vinyl acetate, polyethylene, polypropylene, cellulose derivatives, and many more. In particular cases, the backing layer may be provided with an additional overlay, e.g. by vapour-deposition with metals or other diffusion-blocking additives such as silicon dioxide, aluminium dioxide or similar substances known to those skilled in the art. To improve its outer appearance, the backing layer may also be varnished skin-coloured on the outer side, or treated in some other way.

Dependent on the strength and permeability of the selected material, the thickness of the film-like backing layer usually is 8 to 80 μm. For particular purposes it may, however, also be adjusted to be thicker or thinner than these values.

The detachable protective layer to be removed prior to application of the patch is preferably made up of polyester material (e.g. polyethylene terephthalate film), but any other skin-tolerable plastics may also be used, such as polyvinyl chloride, ethylene-vinyl acetate, vinyl acetate, polyethylene, polypropylene, or cellulose derivatives. In particular cases, vaporization with metals or other diffusion-blocking additives such as silicon dioxide, aluminium oxide and the like may be carried out. In any case, it is necessary to provide a surface coating with dehesive materials, for instance with silicones or fluorine-containing plastics on the side facing the adhesive matrix, for the compound to remain readily detachable.

Especially after a prolonged storage time, slight yellowing can occur in the tulobuterol HCL-containing TTSs;

furthermore, after several months, slight recrystallization was observed as a sign of a certain oversaturation with tulobuterol-HCL. To avoid such unwanted changes, various additives from the field of antioxidants and metal ion complexing agents were tested.

It was found that it is possible to achieve particularly effective suppression of the yellowing by a combination of a phenolic antioxidant and a polyvalent acid (or its salts). As antioxidant, butylhydroxytoluene (BHT) or butylhydroxyanisole (BHA) is utilized with preference. As acids, citric acid or ethylenediaminetetraacetic acid (EDTA) or its salts, such as disodium EDTA are preferably used. It was surprisingly found that by adding the abovementioned antioxidants and complexing agents, not only will the discolouring be suppressed but at the same time there will be no recrystallization.

For this reason it is provided in accordance with the best possible embodiment of the invention that the tulobuterol-containing TTSs contain at least one additive from the group of antioxidants, preferably phenolic compounds, more preferably butylhydroxytoluene or butylhydroxyanisole, as well as in addition at least one further additive from the group of metal ion complexing agents, preferably citric acid or ethylenediaminetetraacetic acid, especially preferred ethylenediaminetetraacetic acid-disodium salt ($Na_2EDTA$).

In the following, the invention will be described by means of examples. These examples do not limit the invention in any way.

EXAMPLES

The examples of transdermal therapeutic systems according to the invention listed in TAB. 1 all have a structure comprising a backing layer, a tulobuterol hydrochloride-containing reservoir layer (as the first matrix layer) and an optionally active substance-free, skin-facing pressure-sensitive adhesive layer. The skin-facing matrix or pressure-sensitive adhesive layer is covered with a removable protective film.

"Optionally active substance-free" means that the skin-facing layer is not loaded with tulobuterol hydrochloride during manufacture and is therefore free of active substance in the initial state. After manufacture and during application, diffusion of the active substance occurs from the reservoir layer through the active substance-free skin-facing layer in the direction towards the skin, followed by the permeation of the active substance through the skin.

To prepare the active substance-containing matrix layers, initially tulobuterol hydrochloride (tulobuterol-HCl) was dissolved in ethanol. Then the other components, including the matrix polymers, were added to this solution, in the suitable amount of usual organic solvents.

The organic solvents were then coated onto a siliconized polyethylene terephthalate film (100 μm thickness) using a hand pull frame for films, and dried for 10 min at 80° C. in the exhaust air oven.

The reservoir layer and skin-facing layer obtained in this manner were mechanically laminated to each other, the protective film of the reservoir layer was removed, and this layer was covered with a polyethylene terephthalate film (15 μm thickness) as permanent backing layer.

The suitability of the examples of application systems prepared according to TAB. 1 for a transdermal therapy with tulobuterol was tested on the model of excised human full-thickness skin. The tests were made using modified permeation cells according to FRANZ at 32° C. in the manner known to those skilled in the art.

Measurements of the quantities of tulobuterol having passed through the skin samples were performed by means of HPLC. The results are shown in FIG. 1.

The values indicated represent the mean value and standard deviation for respective n=3 skin samples.

Examples 1 and 2 show a structure wherein the skin-facing layer in the initial state is active agent-free. After manufacture, diffusion of the active substance takes place into this layer, too. This structure is advantageous in terms of production logistics, the release rates through human skin obtained in vitro are, however, comparatively low since the system as a whole enables only a lower total load with tulobuterol-HCl.

In Examples 3 and 4, tulobuterol-HCl is contained in both layers in equal concentration. The total load is higher than in Examples 1 and 2. This is also reflected in a markedly increased release performance in vitro.

Example 3 is slightly superior to Example 4 in respect of its release rate. The slightly lower portion of Budragit® E100 compared to Example 4 obviously at the same has a positive effect on the release performance.

It should be emphasized that in all four examples a linear release behaviour is obtained for the active agent tulobuterol which is maintained for at least up to 72 h (FIG. 1).

Example 5 shows a formulation corresponding to the best possible embodiment of the invention. Both the skin-facing layer as well as the reservoir layer contain a combination of a phenolic antioxidant (butylhydroxytoluene, BHT) and ethylenediaminetetraacetic acid (disodium salt), which results in a reliable prevention of the yellowing of the TTSs and of the recrystallization of the active substance tulobuterol during the period of storage.

TABLE 1

| Example No. | Weight Per Unit Area [g/m²]** | Reservoir Layer Components | % | Skin-Facing Layer | % |
|---|---|---|---|---|---|
| 1 | 154.3 | Tulobuterol-HCl | 11.6 | Tulobuterol-HCl | — |
|   |   | Eudragit ® E100 | 13.7 | Eudragit ® E100 | 10.0 |
|   |   | Durotak ® 2287* | 74.7 | Durotak ® 2287* | 77.5 |
|   |   | Oleic Acid | — | Oleic Acid | 12.5 |
| 2 | 166 | Tulobuterol-HCl | 16.3 | Tulobuterol-HCl | — |
|   |   | Eudragit ® E100 | 19.3 | Eudragit ® E100 | 10.0 |
|   |   | Durotak ® 2287* | 64.4 | Durotak ® 2287* | 72.7 |
|   |   | Oleic Acid | — | Oleic Acid | 17.3 |
| 3 | 162.1 | Tulobuterol-HCl | 11.6 | Tulobuterol-HCl | 11.6 |
|   |   | Eudragit ® E100 | 13.7 | Eudragit ® E100 | 15.1 |
|   |   | Durotak ® 2287* | 68.5 | Durotak ® 2287* | 67.1 |
|   |   | Oleic Acid | 6.2 | Oleic Acid | 6.2 |
| 4 | 171.3 | Tulobuterol-HCl | 11.6 | Tulobuterol-HCl | 11.6 |
|   |   | Eudragit ® E100 | 15.1 | Eudragit ® E100 | 15.1 |
|   |   | Durotak ® 2287* | 67.1 | Durotak ® 2287* | 67.1 |
|   |   | Oleic Acid | 6.2 | Oleic Acid | 6.2 |
| 5 | 159.0 | Tulobuterol-HCl | 11.6 | Tulobuterol-HCl | 11.6 |
|   |   | Eudragit ® E100 | 13.7 | Eudragit ® E100 | 15.1 |
|   |   | Durotak ® 2287* | 67.9 | Durotak ® 2287* | 67.1 |
|   |   | Oleic Acid | 6.2 | Oleic Acid | 6.2 |
|   |   | BHT | 0.1 | BHT | 0.1 |
|   |   | $Na_2EDTA$ | 0.5 | $Na_2EDTA$ | 0.5 |

*cross-linked by aluminium ions (0.05 mass percent)
**relative to the sum of reservoir layer and skin-facing layer BHT=butylhydroxytoluene;
$Na_2HDTA$=ethylenediaminetetraacetic acid, disodium salt.

The percentages given in the table refer to mass portions (m/m), relative to the total mass of the respective matrix layer.

What is claimed is:

1. A transdermal therapeutic system comprising:
a largely water vapour-impermeable backing layer,
at least one active substance-containing matrix layer comprising the active substance tulobuterol, and
a removable protective layer,
wherein said matrix is based on polyacrylate pressure-sensitive adhesives and contains tulobuterol in the form of its salt tulobuterol hydrochloride as the active substance, and said matrix contains a polymer having amino-functional groups in its side chains.

2. The transdermal therapeutic system according to claim 1 wherein the mass content of tulobuterol hydrochloride is 2.5 to 20%, relative to the mass of the active substance-containing matrix.

3. The transdermal therapeutic system according to claim 1, wherein the mass content of said polymer is 2 to 20%, relative to the mass of the active substance-containing matrix.

4. The transdermal therapeutic system according to claim 1, wherein as the polymer having amino-functional groups a butyl methacrylate-(2-dimethylaminoethyl)-methyl methacrylate copolymer is used.

5. The transdermal therapeutic system according to claim 1, wherein the system also comprises a second tulobuterol hydrochloride-containing matrix layer.

6. The transdermal therapeutic system according to claim 1, wherein in the state immediately after its manufacture the system comprises at least one further matrix layer based on a polyacrylate pressure-sensitive adhesive, which layer does not contain active substance.

7. The transdermal therapeutic system according to claim 1, wherein the system contains permeation-enhancing additives.

8. The transdermal therapeutic system according to claim 1, wherein the system contains one or more fatty acids in the matrix layer, said fatty acid(s) being contained in a concentration of 2 to 20%, relative to the total mass of the matrix.

9. The transdermal therapeutic system according to claim 1, wherein the system enables the transdermal administration of common daily doses from 0.5 up to maximally 6 mg, of tulobuterol hydrochloride over an application period of at least 3 days.

10. The transdermal therapeutic system according to claim 1, wherein at least one matrix layer contains one or more additional pharmaceutically active substances.

11. The transdermal therapeutic system according to claim 1, wherein the weight per unit area of the active substance-containing matrix is at least 120 g/m$^2$.

12. The transdermal therapeutic system according to claim 1, wherein the system contains at least one additive comprising an antioxidant.

13. The transdermal therapeutic system according to claim 12, wherein the system contains at least one further additive comprising a metal ion complexing agent.

14. The transdermal therapeutic system according to claim 1, wherein the matrix contains 67% or greater of polyacrylate pressure- sensitive adhesives.

15. A method for the treatment of asthma and related forms of disease, which comprises:
applying to the skin of a person affected by one of said diseases a transdermal therapeutic system according to claim 1.

16. The transdermal therapeutic system according to claim 8, wherein said fatty acid(s) are at least one compound selected from the group consisting of lauric acid, myristic acid and oleic acid.

17. The transdermal therapeutic system according to claim 12, wherein said antioxidant comprises a phenolic compound that is butylhydroxytoluene or butylhydroxyanisole.

18. The transdermal therapeutic system according to claim 13, wherein said metal ion complexing agent comprises citric acid, ethylenediaminetetraacetic acid or ethylenediaminetetraacetic acid-disodium salt (Na$_2$EDTA).

19. The transdermal therapeutic system according to claim 1, wherein the mass content of tulobuterol hydrochloride is 5 to 10%, relative to the mass of the active substance-containing matrix.

20. The transdermal therapeutic system according to claim 1, wherein the active substance-containing matrix contains a polymer having amino-functional groups in its side chains and that the mass content of said polymer is 10 to 16%, relative to the mass of the active substance-containing matrix.

21. The transdermal therapeutic system according to claim 1, wherein the system contains one or more fatty acids in the matrix layer, said fatty acid(s) being contained in a concentration of 5 to 10%, relative to the total mass of the matrix.

22. A transdermal therapeutic system comprising:
a largely water vapour-impermeable backing layer,
at least one active substance-containing matrix layer comprising the active substance tulobuterol, and
a removable protective layer,
wherein said matrix is based on polyacrylate pressure-sensitive adhesives and contains tulobuterol in the form of its salt tulobuterol hydrochloride as the active substance, and the system also comprises a second tulobuterol hydrochloride-containing matrix layer.

23. A transdermal therapeutic system comprising:
a largely water vapour-impermeable backing layer,
at least one active substance-containing matrix layer comprising the active substance tulobuterol, and
a removable protective layer,
wherein said matrix is based on polyacrylate pressure-sensitive adhesives and contains tulobuterol in the form of its salt tulobuterol hydrochloride as the active substance, and in the state immediately after its manufacture the system comprises at least one further matrix layer based on a polyacrylate pressure-sensitive adhesive, which layer does not contain active substance.

24. A transdermal therapeutic system comprising:
a largely water vapour-impermeable backing layer,
at least one active substance-containing matrix layer comprising the active substance tulobuterol, and
a removable protective layer,
wherein said matrix is based on polyacrylate pressure-sensitive adhesives and contains tulobuterol in the form of its salt tulobuterol hydrochloride as the active substance, and the system permits the transdermal administration of common daily doses from 0.5 up to maximally 6 mg, of tulobuterol hydrochloride over an application period of at least 3 days.

25. A transdermal therapeutic system comprising:
a largely water vapour-impermeable backing layer,
at least one active substance-containing matrix layer comprising the active substance tulobuterol, and
a removable protective layer, wherein said matrix is based on polyacrylate pressure-sensitive adhesives and contains tulobuterol in the form of its salt tulobuterol hydrochloride as the active substance, and at least one matrix layer contains one or more additional pharmaceutically active substances.

26. A transdermal therapeutic system comprising:
a largely water vapour-impermeable backing layer,
at least one active substance-containing matrix layer comprising the active substance tulobuterol, and
a removable protective layer,
wherein said matrix is based on polyacrylate pressure-sensitive adhesives and contains tulobuterol in the form of its salt tulobuterol hydrochloride as the active substance, and the weight per unit area of the active substance-containing matrix is at least 120 $g/m^2$.

* * * * *